(12) United States Patent
Franco Nardo et al.

(10) Patent No.: US 8,313,452 B2
(45) Date of Patent: Nov. 20, 2012

(54) DEVICE AND MACHINE FOR REGENERATING A HUMAN LIVER

(75) Inventors: Bruno Pasquale Franco Nardo, Bologna (IT); Antonino Cavallari, Ponticella di San Lazzaro di Savena (IT); Domenico Cianciavicchia, Cavuccio (IT)

(73) Assignee: Bellco S.r.l., Mirandola (Modena) (IT)

( * ) Notice: Subject to any disclaimer, the term of this patent is extended or adjusted under 35 U.S.C. 154(b) by 0 days.

(21) Appl. No.: 13/050,044

(22) Filed: Mar. 17, 2011

(65) Prior Publication Data

US 2011/0166493 A1 Jul. 7, 2011

Related U.S. Application Data

(62) Division of application No. 10/553,174, filed as application No. PCT/IB2004/001142 on Apr. 15, 2004, now abandoned.

(30) Foreign Application Priority Data

Apr. 18, 2003 (IT) ................ BO2003A0239

(51) Int. Cl.
*A61M 37/00* (2006.01)
*A61M 31/00* (2006.01)

(52) U.S. Cl. ............ 604/6.14; 604/8; 604/508

(58) Field of Classification Search ........ 604/6.14, 604/8, 500, 507–509, 6.11, 6.13
See application file for complete search history.

(56) References Cited

U.S. PATENT DOCUMENTS

| 4,192,302 A * | 3/1980 | Boddie ............ 604/5.04 |
| 4,865,583 A | 9/1989 | Tu |
| 4,950,230 A | 8/1990 | Kendell |
| 5,282,466 A | 2/1994 | Duffy et al. |
| 5,368,555 A | 11/1994 | Sussman et al. |
| 5,449,342 A | 9/1995 | Hirose et al. |
| 5,800,374 A | 9/1998 | Beyersdorf |
| 6,336,910 B1 | 1/2002 | Ohta et al. |
| 6,602,468 B2 * | 8/2003 | Patterson et al. ............ 422/45 |
| 6,699,231 B1 * | 3/2004 | Sterman et al. ............ 604/509 |
| 6,913,588 B2 | 7/2005 | Weitzel et al. |
| 2002/0077581 A1 | 6/2002 | Davidner et al. |
| 2007/0051681 A1 | 3/2007 | Nardo et al. |

FOREIGN PATENT DOCUMENTS

| DE | 19823146 C1 | 7/1999 |
| EP | 0364799 A2 | 5/1995 |
| EP | 1132101 A1 | 9/2001 |

OTHER PUBLICATIONS

International Search Report and Written Opinion issued in PCT/IB2004/001142, mailed Mar. 3, 2003, 5 pages.

* cited by examiner

*Primary Examiner* — Kevin C Sirmons
*Assistant Examiner* — Imani Hayman
(74) *Attorney, Agent, or Firm* — Faegre Baker Daniels LLP

(57) ABSTRACT

A method of assisting in regenerating a patient's liver includes fluidly coupling a first end of a conduit with a first blood vessel of the patient that carries oxygenated blood. A second end of the conduit is fluidly coupled with a second blood vessel of the patient that carries blood to the patient's liver. Oxygenated blood is allowed to flow from the first blood vessel, through the conduit and to the liver via the second blood vessel of the patient.

7 Claims, 5 Drawing Sheets

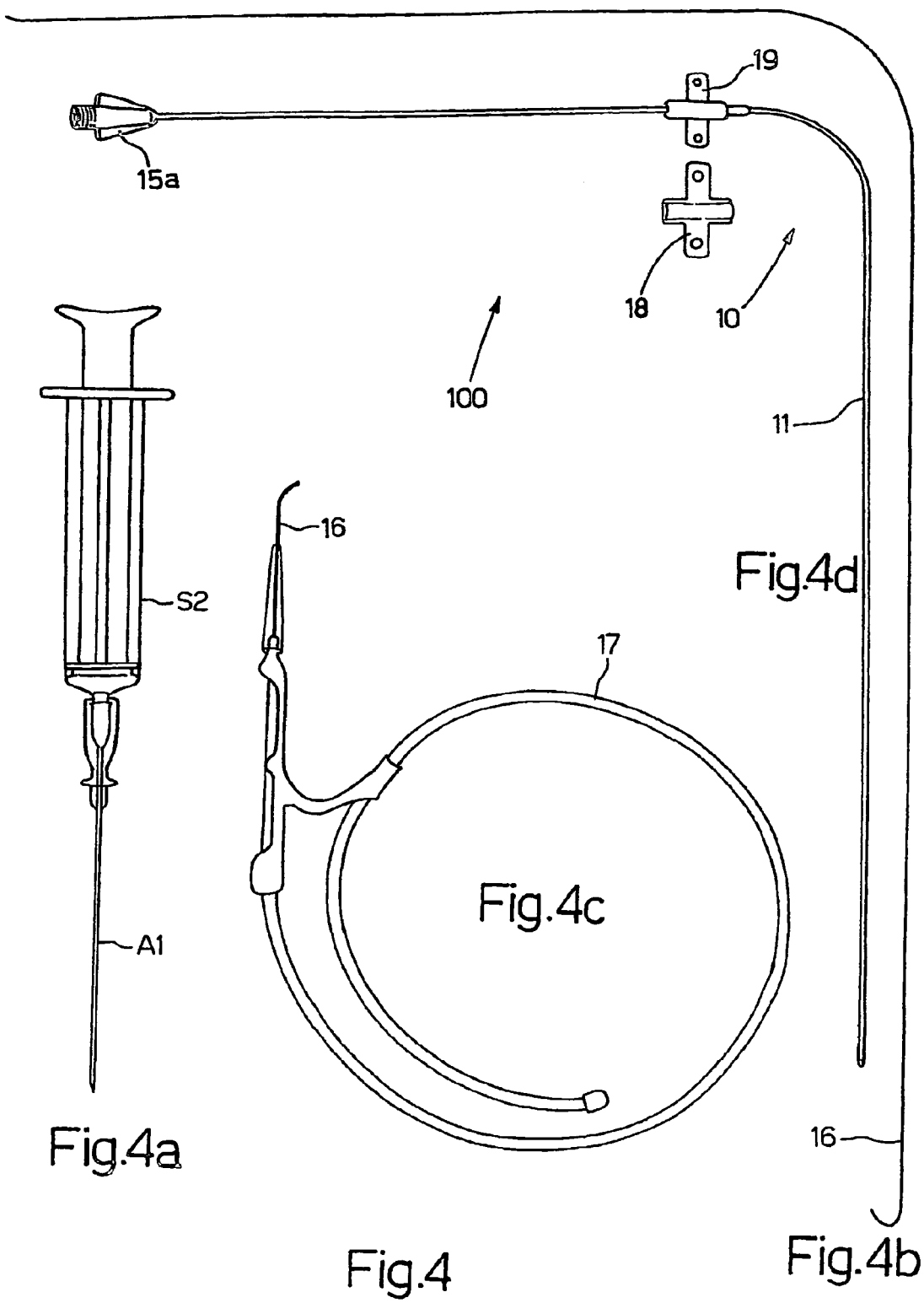

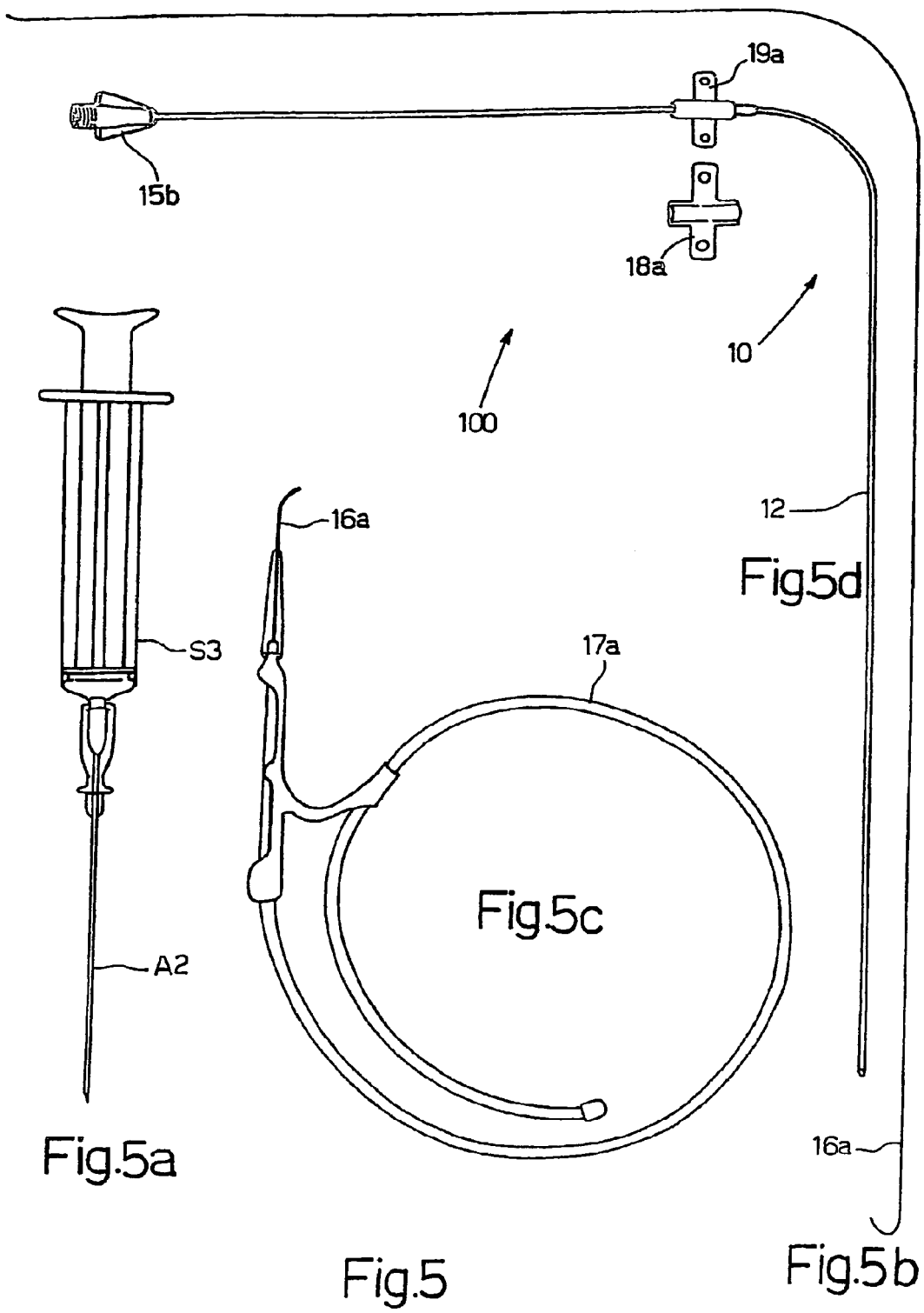

DEVICE AND MACHINE FOR REGENERATING A HUMAN LIVER

CROSS-REFERENCES TO RELATED APPLICATIONS

This application is a divisional of U.S. application Ser. No. 10/553,174, filed Oct. 13, 2006, which is a national stage entry of PCT/IB2004/001142, filed Apr. 15, 2004, which claims priority to Italian Application No. BO2003A000239, filed Apr. 18, 2003, all of which are incorporated herein by reference in their entirety.

TECHNICAL FIELD

The present invention relates to a process, and to a machine implementing said process, for regeneration of a human liver through treatment with oxygenated blood. This treatment may comprise hyperoxygenation of the portal venous blood.

The present invention also relates to a device for arterialization of the portal vein and to a relative kit for its application to the body of a patient.

BACKGROUND ART

It is known that acute hepatic insufficiency is a serious clinical syndrome that may be caused by various etiologic factors (toxic, viral, vascular occlusion, low flow rate, etc.). These factors all have the common characteristic of causing variable degrees of necrosis of the hepatocytes. In the massive form in which over 80% of the hepatocytes are destroyed the prognosis is unfavourable unless a liver transplant is performed quickly. On the other hand, it is known that a liver transplant cannot always be performed (for example, due to sepsis, or to the advanced age of the patient, etc.) and, even when a transplant is indicated, it cannot always take place due to the shortage of donors.

On the other hand, current support systems, among which the "bio-artificial liver", are essentially purifying and do not promote hepatic regeneration, but are only useful while waiting for an organ to become available or until the necrotic liver undergoes a process of self-regeneration which would avoid transplant.

Instead, to promote hepatic regeneration the present invention proposes (in a particular embodiment) arterialization of the portal vein, or, in other words, oxygenation of portal blood with arterial blood.

Surgical arterialization of the portal vein has proved efficacious both clinically, where it has been used to solve massive hepatic necrosis secondary to arterial thrombosis after transplant, and in an experimental model in the rat in which massive hepatic necrosis was induced by means of administering carbon tetrachloride.

As will be explained in greater detail hereunder, oxygenation of the portal blood is performed by means of a specific device that can be marketed equipped with a relative kit to be implanted in the body of the patient (see below).

Moreover, on the basis of experimental data, by oxygenating the portal vein according to the present invention, hepatic necrosis is resolved completely within forty-eight hours, although a great improvement can already be observed after twenty-four hours.

It is known that all the blood of the intestine flows through the portal vein. The portal vein (also called "portal trunk") originates from the union of its roots represented by the superior mesenteric vein and the inferior mesenteric vein, which collect blood from the intestine, and by the splenic vein which instead conveys the blood coming from the spleen. Being venous blood, it is therefore poorly oxygenated. This blood, which, as mentioned, comes from the intestine and the spleen, is metabolized by the liver and returned to the vena cava. Therefore, in the liver as well as the arterial flow route (hepatic artery), there is also a venous flow route (portal vein) and a discharge route (the suprahepatic veins which discharge into the vena cava). The blood reaches the right heart through the vena cava.

It has been experimentally observed that hyperoxygenation of the portal blood stimulates hepatic regeneration. In other words, the liver is an organ capable of regeneration. Therefore, in the presence of necrosis caused by the action of toxic agents, of viral agents or by mushroom poisoning, if oxygenated blood reaches the portal system hepatic necrosis is resolved in 48 hours through triggering of cellular regeneration.

There are two routes through which the liver can be reached:
(1) through the jugular vein; or
(2) by direct injection of the liver.

It is known that the jugular vein carries blood to the right heart. To reach the portal vein it is possible, through the jugular vein and the right atrium, to reach the suprahepatic vena cava and the suprahepatic veins (usually right or middle). Therefore, a direct link is created with the portal branch (usually right) and the portal trunk.

Arterial blood, taken for example from the femoral artery at the groin, is at high pressure (100-120 mm of mercury) and ends up in a low pressure portal venous system (15-20 mm of mercury), so that a sort of "natural pumping" of arterial blood towards the portal vein is obtained.

DISCLOSURE OF INVENTION

Therefore, the principal object of the present invention is a device for arterialization of the portal vein according to the characteristics claimed in claim 1.

A further object of the present invention is a kit for application of this device to the body of a patient according to the characteristics claimed in claim 6.

Moreover, further objects of the present invention are a method for regeneration of a human liver and a relative machine to carry out said method. The innovative method and the machine are claimed in corresponding independent claims.

BRIEF DESCRIPTION OF THE DRAWINGS

The present invention shall now be described with reference to the accompanying drawings, which show some non-limiting embodiments, in which:

FIGS. 4 and 5 shows some components of the device according to the present invention and of the kit designed for application of this device to the body of a patient;

BEST MODE CARRYING OUT OF INVENTION

In the accompanying FIGS. 1-5, the number 10 indicates a device for arterialization of the portal vein according to the present invention.

To fully understand the present invention it is firstly necessary to describe some parts of the human body B.

Therefore, in the human body B the liver L, the heart H, the portal vein VP, the vena cava VC, the jugular vein VG and the femoral artery AF can be distinguished.

In this first particular embodiment, to reach the portal vein VP a catheter 11 has been used which, with means to be described in more detail hereunder, is inserted into the jugular vein VG and reaches the heart H after passing through the vena cava VC. From the heart H the catheter 11 is then made to advance towards the portal vein VP.

Figure 6:
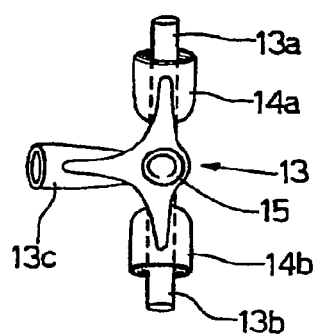
FIG. 6 shows a further component, enlarged, of the kit for application of the device for arterialization shown in FIG. 1 to the body of a patient.

The device also comprises a second catheter 12, which reaches the femoral artery AF with a three-way connection 13, represented in greater detail in FIG. 6.

Figure 1:
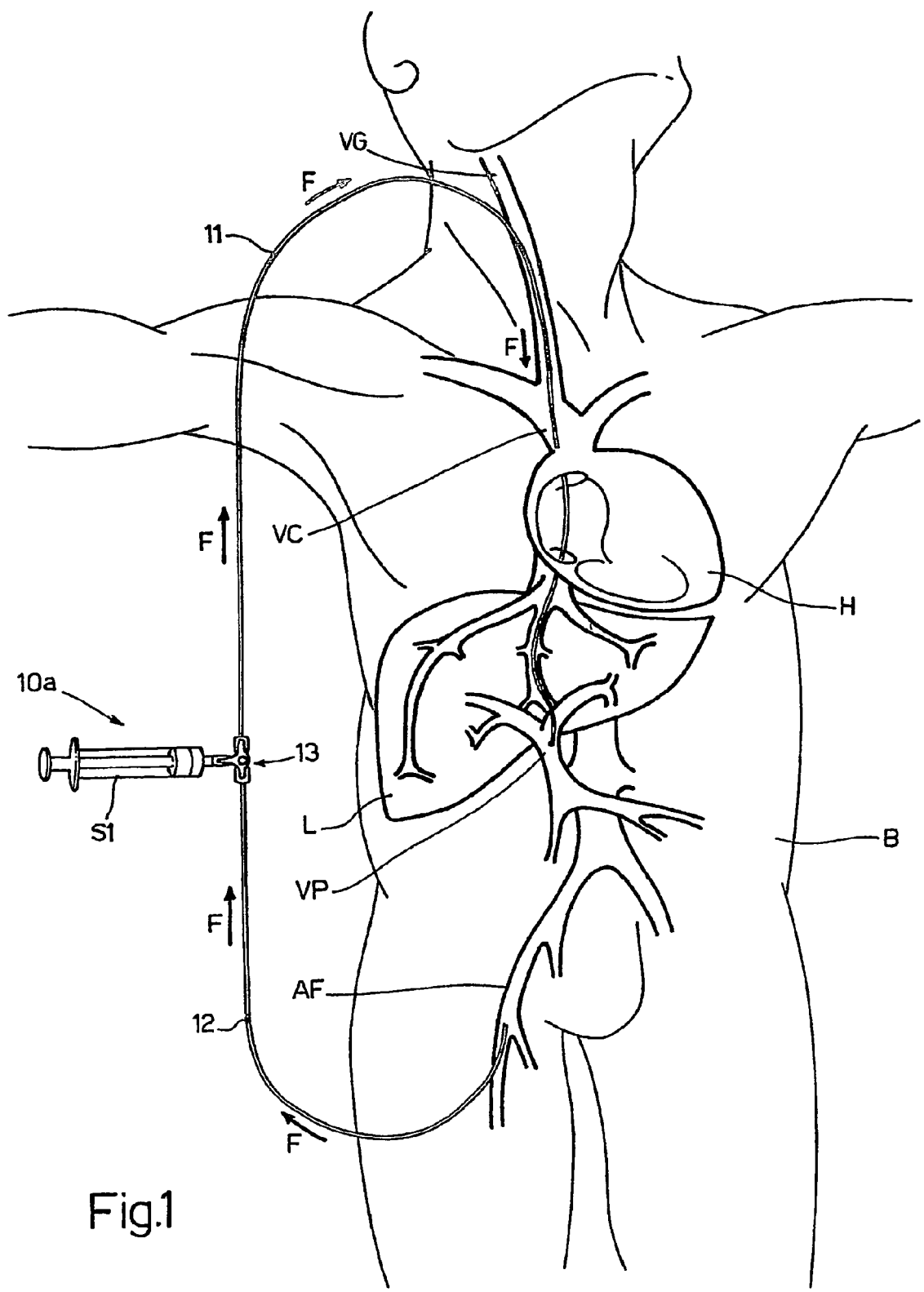
FIG. 1 shows a device according to the present invention applied to a human body.

As shown again in FIG. 1, by means of the device 10 the arterial blood coming from the femoral artery AF is conveyed towards the portal vein VP running through the catheters 12 and positioned in succession with each other, according to a direction identified by an arrow F.

For the reasons mentioned previously, oxygenation of the portal vein VP by arterial blood taken from the femoral artery AF induces rapid regression of necrosis of the liver L.

As shown again in FIG. 1 the device 10 is not provided with pumping means as blood is pumped naturally, being delivered from the femoral artery AF with a pressure of 100-120 mm of mercury to flow towards a zone, the portal vein VP, with a pressure of 10-15 mm of mercury.

As shown in greater detail in FIG. 6, the three-way connection 13 comprises three tubular elements 13a, 13b, 13c which may be obtained in one piece. In particular, the tubular element 13a is, so as to speak, the ideal continuation of the tubular element 13b, while the tubular element 13c is positioned perpendicularly to the first two so that the three-way connection 13 is in the shape of a T. The tubular elements 13a, 13b and 13c are connected to one another hydraulically.

Moreover, the tubular elements 13a, 13b are each provided with a relative threaded connection capsule 14a, 14b that can be screwed onto a respective threaded connection element 15a, 15b positioned at one end of the respective catheter 11, 12 (see FIGS. 4-6). In other words, by screwing a respective threaded capsule 14a, 14b onto the respective threaded connection element 15a, 15b the catheters 11, 12 are fixed to the three-way connection 13. In this way the catheters 11, 12 are connected hydraulically to the connection 13.

The end of a syringe S1 is inserted into the tubular element 13c, to allow the operator to ensure the catheters 11, have been inserted correctly into the portal vein VP and femoral artery AF respectively, as shall be seen below.

As shown in FIG. 6 the three-way connection 13 also has a tap 15, which is positioned by the operator to allow according to choice:

hydraulic connection in series of the two catheters 11, 12;
hydraulic connection of the sole catheter 11 to the syringe S1; or
hydraulic connection of the sole catheter 12 to the syringe S1.

Figure 3:
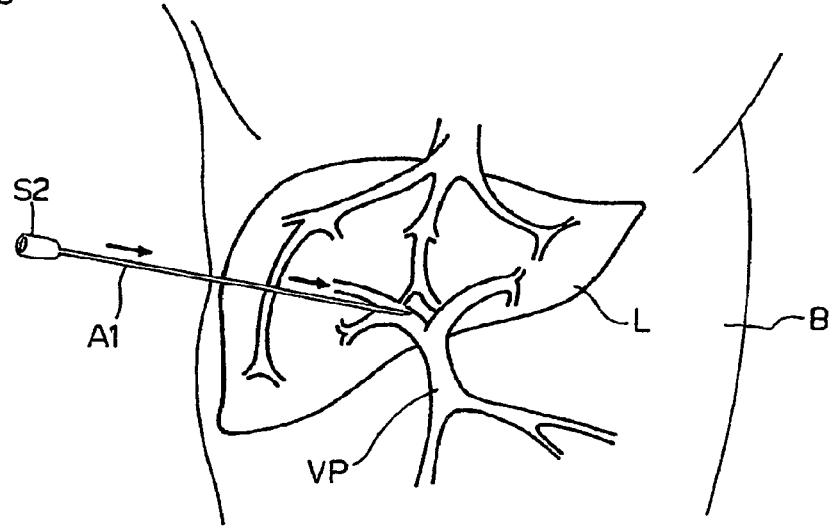
FIG. 3 shows a second alternative way of reaching the portal vein.

The operator will choose the position of the tap 15 as a function of the treatment phases of the patient (see below). FIG. 3 shows, as an example, a further means of reaching the portal vein VP. In this case the portal vein VP has been reached using a needle A1 of a syringe S2.

FIGS. 4 and 5 show other elements that are part of a kit 100 for application of the device 10 to the body of a patient.

In particular, FIG. 4 shows the elements relative to the catheter 11, while FIG. 5 shows the elements used to insert the catheter 12 into the body B. The elements relative to the two catheters 11 and 12 are similar and at times may even be identical (see below).

If, for example, we consider the elements relative to the catheter 11 we can see that there is a metal guide 16 with radiopaque markers. The metal guide 16 has a diameter of 0.8 mm with a straight and soft tip at one end and in the shape of a J at the other end.

This metal guide 16 is pushed inside the body B by means of a feed device 17 around which the operator squeezes his/her fingers, using the thumb to make the metal guide 16 move forward.

FIG. 4a shows a syringe S2 provided with a needle A1, preferably, although not necessarily, of the 18 Ga gauge.

As shown in FIG. 4d, the catheter 11 is also provided with a clamp 18 and a supporting element 19, which may be fixed to the skin of the patient by suture stitches. The purpose of the clamp 18 is to protect the catheter 11 and hold it to the skin at its exit point from the body.

The catheter 11 is made of polyurethane, it is radiopaque to allow its position in the body B to be checked, and it is heparinized to prevent clots from forming and clogging it. The internal gauge of the catheter must not exceed 18 Ga.

The process for introducing the catheter 11 is as follows:

(A) Transjugular access (FIGS. 1 and 2):
  (a1) the syringe S2 is filled with a saline solution connected to an angiocath with needle; after being inserted into the right jugular vein VG aspiration is performed until venous blood, easily distinguished by an expert, is visible; it is mentioned by way of parenthesis that the angiocath is a venous catheter available on the market and used both for arterial and venous vascular access, while saline solution is used to improve aspiration of the blood and prevent the introduction of air bubbles;
  (a2) the body of the syringe S2 is detached and the metal guide 16 is inserted into the lumen of the needle A1; the metal guide 16 is made to slide, utilizing in this operation the device 17;
  (a3) the metal guide 16 moves through the inferior vena cava VC, the right suprahepatic vein and the portal vein VP; the metal guide 16 is blocked with one of its ends at the portal vein VP;
  (a4) the needle A1 is removed by sliding it towards the outside of the metal guide 16;
  (a5) the metal guide 16 is inserted into the catheter 11 and the latter is made to slide on the metal guide 16 until one end of the catheter 11 reaches the portal vein VP; as the catheter 11 is radiopaque, it is possible to constantly monitor its route through the body B of the patient using radiological observation;
  (a6) the metal guide 16 is removed from the catheter 11;
  (a7) the catheter 11 is connected to the three-way connection 13, with suitable positioning of the tap 15;
  (a8) the three-way connection 13 is connected to the syringe S1 (FIG. 1) and blood is aspirated to confirm that it is effectively portal blood.

(B) Percutaneous hepatic access (FIG. 3):
  (b1) a syringe filled with saline solution is prepared connected to an angiocath with needle;
  (b2) the skin and hepatic parenchyma are pierced with a needle A1 until portal blood is aspirated;
  (b3) the metal guide 16 is inserted until reaching the portal vein VP;
  (b4) the catheter 11 is introduced using the set 100 with the system described previously;

(b5) aspiration is performed to ensure that it is effectively portal blood;
(b6) the three-way catheter 13, is connected, with suitable positioning of the tap 15; and
(b7) the three-way tap 13 is connected to the syringe S1 (FIG. 1) and blood is aspirated to confirm that it is effectively portal blood.

As well as being radiopaque and heparinized, the properties of the catheter 11 must allow it to remain in the lumen of the portal vein VP for at least twenty-four hours. The gauge of the catheter 11 must be between 1.5 mm and 2.5 mm.

The length of the catheter 11 introduced percutaneously into the abdomen and through the liver L (FIG. 3) must be at least 70 cm.

In the case in FIG. 3, the needle A1 must be around 30 cm in length and have a thickness of 18 Ga. If the catheter 11 is introduced from the jugular vein VG (FIGS. 1 and 2) the needle is around 15 cm in length.

The arterial catheter 12 shown in FIG. 3 is designed to access the arterial system by cannulating the femoral artery AF at the groin (FIG. 1), or through the carotid (right or left).

The other elements shown in FIG. 5 that are utilized to introduce the catheter 12 may be identical to the elements in FIG. 4 referring to the catheter 11.

Figure 2:
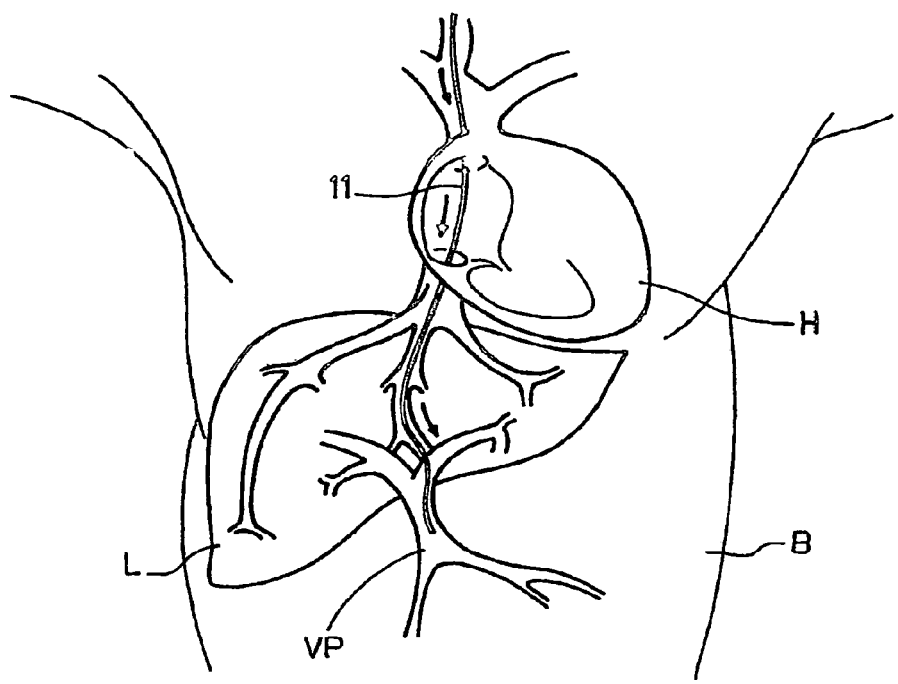
FIG. 2 shows a first method of reaching the portal vein also shown in FIG. 1.

Therefore, to summarize, the possible variants relative to the arterial and venous vascular accesses are as follows:
(a) right (or left) femoral artery with right jugular vein (FIGS. 1, 2);
(b) right (or left) femoral artery with transhepatic percutaneous catheter (FIG. 3);
(c) right (or left) common carotid artery with right jugular vein; and
(d) right (or left) common carotid artery with transhepatic percutaneous artery.

The kit 100 forming a further object of the present invention may be composed of the following elements:
(i) two radiopaque and heparinized catheters 11, 12; it is mentioned by way of parenthesis that the catheter 12, as shown in FIG. 5, is also provided with a clamp 18a and a supporting element 19a;
(ii) two metal guides 16, 16a (FIG. 5) for insertion of the catheters 11, 12;
(iii) two syringes S2, S3, each with a respective needle A1, A2; in particular, the kit 100 may be provided with two needles A1 having different diameters according to the route chosen for insertion of the catheter 11;
(iv) two feed devices 17, 17a (see also FIG. 5) for the guides 16, 16a;
(v) a three-way connection 15; and
(vi) a syringe S1.

If necessary, the kit 100 may also be equipped with a device (not shown) to heat the arterial blood travelling through the catheters 11 and 12 to avoid the danger of clots.

The advantages of the device 10 and the relative kit 100 are many.

They are essentially due to the fact that they allow rapid positioning of the catheters 11, 12 in order to obviate in extremely quick times occurring problems of liver necrosis.

The elements of which the kit 100 is composed may be sold in a pack (not shown) of transparent plastic material having the prescribed requirements relative to hygiene.

The blood travelling through the two catheters 11, 12 should have no problems of coagulation. In any case, as mentioned, the kit 100 may be completed with a device (not shown) in the form of a sleeve provided with heating elements, if necessary electric, to heat the portions of the catheters 11, 12 outside the body B.

Figure 7:
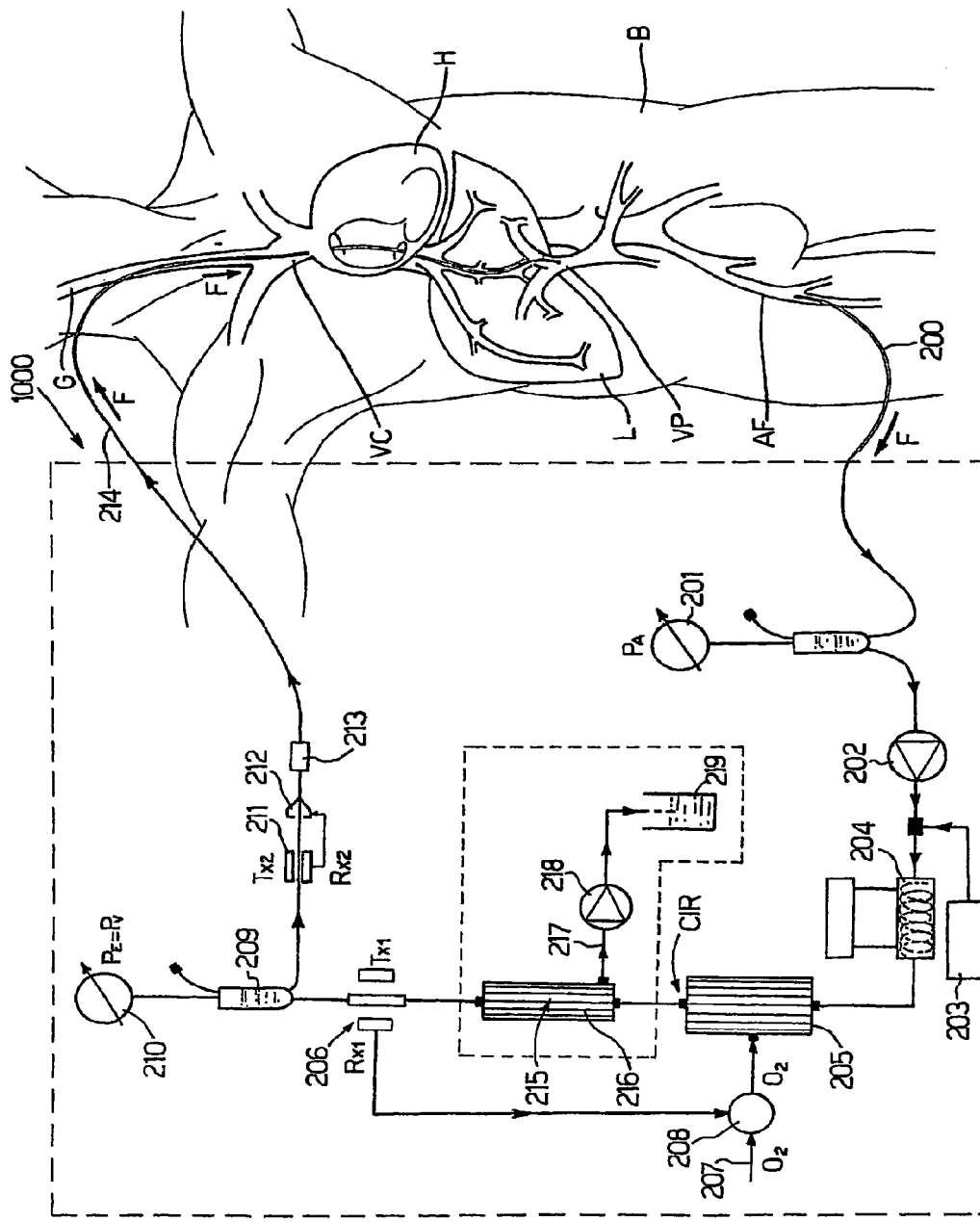
FIG. 7 represents a machine to efficaciously induce regeneration of a human liver through the supply of oxygenated blood thereto.

To increase the efficacy of the treatment described hereinbefore a machine 1000, represented in FIG. 7, has been devised.

In the embodiment in FIG. 7, the machine 1000 is connected to the body B in the manner described with reference to FIG. 1.

The machine 1000 has an extracorporeal circuit CIR to take arterial blood comprising, in turn, a plurality of tubes. The machine 1000 is utilized to treat the blood and to return this blood to the portal vein VP to obtain regeneration of the liver L.

In the example shown in FIG. 7 the arterial blood is taken from the femoral artery AF by means of a catheter 200, as already described with reference to FIG. 1.

A device 201 to measure the arterial pressure is provided immediately downstream of the catheter 200. This device 201, in a known way, is utilized to measure the aspiration arterial pressure. In fact, it is known that if the catheter 200 becomes attached to the vessel wall and bursts it, this produces a very high negative pressure. It is therefore necessary have the device 201 available to detect any negative pressure produced in the point in which the catheter 200 is inserted into the human body B.

Continuing to analyze the elements constituting the machine 1000 positioned in series in the extracorporeal circuit CIR, we can see a pumping system 202 (preferably of the peristaltic type) followed by a device 203 for introduction of an anticoagulant fluid, such as heparin.

Downstream of the device 203 a coil heater 204 may be provided to keep the blood at a pre*¥stablished temperature (35-36° C.) and to prevent it from coagulating. The coil heater 204 is particularly useful if the blood flow rates are high (around 400-500 cc/min), while for low flow rates (around 100 cc/min), as in the cases commonly taken into consideration in the treatments contemplated in the present invention, the coil heater 204 may be omitted.

Advancing in the direction of flow of the blood, positioned after the coil heater 204 is an oxygenation device 205 designed to introduce oxygen in the form of O2 into the blood in extracorporeal circulation.

Introduction of oxygen into the blood by means of the oxygenation device 205 is controlled in feedback by means of a control device 206 that measures both hematocrit and saturation, expressed in terms of partial pressure of the molecular oxygen in the blood. In a known way the control device 206 comprises a transmitter element Tx1 and a receiver element Rx1.

In other words, the device 206 measures some important parameters of the blood to understand the degree of oxygenation thereof. As a function of said parameters the device 206 regulates the quantity of oxygen flowing from a supply line 207 towards the oxygenation device 205 by controlling the degree of aperture of a valve 208.

The extracorporeal circuit CIR also comprises a drip chamber 209 to capture air in the form of bubbles to which a device 210 to measure the portal vein VP pressure is connected.

The circuit CIR is completed with equipment 211 to control gaseous embolism, a clamp 212 to interrupt blood flow towards the body B and an infusion point 213 through which it is possible to introduce into the circuit CIR any substances useful for the treatment being carried out. Also in this case, in a known way, the equipment 211 comprises a transmitter element Tx2 and a receiver element Rx2 to detect the presence of air bubbles.

If the equipment 211 should detect the presence of air bubbles in the blood in extracorporeal circulation, it would immediately give the alarm and automatically close the clamp 212. Moreover, by means of an aspiration syringe (not shown) the operator will, in a known way, aspirate the air bubble into the drip chamber 209 from where it will be evacuated from the circuit CIR. Simultaneously an electronic control unit (not shown), which will supervise all the previously described operations, will also interrupt operation of the pumping system 202.

Obviously, the equipment 1000 is also provided with a second catheter 214 to return treated blood to the body B, in particular to the portal vein vP, with the procedure described hereinbefore with reference to FIG. 1.

It is also obvious that the equipment 1000 may advantageously be employed also in the case of blood being returned directly to the liver L, as has already been described with reference to FIG. 3.

Moreover, it is known how in some pathologies, also of hepatic origin, there is an accumulation of liquid due to a decrease in pressure in the corporeal circuit. It is therefore necessary to remove the plasma water from the blood in extracorporeal circulation in the circuit CIR.

For this purpose a hemofiltration device 215 has been provided in which plasma filtration of the blood takes place. The device 215 comprises, in turn, a filter 216, an evacuation tube 217, a peristaltic pump 218 designed to evacuate the plasma water, which is collected in a container 219. In this way a higher concentration of hemoglobulin is obtained, simultaneously obtaining greater blood oxygenation. The filter 216 comprises, in a known way, a semi-permeable membrane (not shown) through which the blood yields the plasma water which, as already mentioned, is aspirated by the pump 218 through the evacuation tube 217.

Therefore, in other words, in an innovative way, a hemofiltration circuit designed to remove plasma water from the blood in extracorporeal circulation has been added to the previously disclosed extracorporeal oxygenation circuit for blood, which essentially utilizes the circuit CIR.

The disposable elements of the machine 1000 may be the catheters 200, 214, the tubes constituting the circuit CIR, the oxygenation device 205, the filter 216, the plasma water evacuation tube 217, the container 219 and the drip chamber 209.

The invention claimed is:

1. A method of assisting in regenerating a patient's liver, the method comprising steps of:
    fluidly coupling a first catheter with an artery of the patient;
    fluidly coupling a second catheter with the patient's portal vein;
    fluidly coupling an extracorporeal circuit between the first catheter and the second catheter such that blood exiting the artery of the patient passes through the first catheter, through the extracorporeal circuit and returns to the patient's portal vein and into the patient's liver through the second catheter;
    monitoring at least one of a hematocrit and a partial pressure of molecular oxygen in the blood flowing through the extracorporeal circuit; and
    using feedback control to regulate how much oxygen is provided to an oxygenator configured to provide oxygen to the blood flowing through the extracorporeal circuit.

2. The method of claim 1, wherein fluidly coupling the second catheter with the patient's portal vein comprises steps of:
    advancing a wire guide through the patient's right jugular vein, inferior vena cava and right suprahepatic vein;
    advancing the second catheter over the wire guide; and
    removing the wire guide.

3. The method of claim 1, wherein the extracorporeal circuit further comprises a heater.

4. The method of claim 1, wherein the extracorporeal circuit further comprises a hemofilter.

5. The method of claim 1, wherein the extracorporeal circuit further comprises a drip chamber.

6. The method of claim 1, wherein the extracorporeal circuit further comprises a pump.

7. The method of claim 1, wherein the extracorporeal circuit further comprises a blood oxygen sensor.

* * * * *